(12) United States Patent
Kang et al.

(10) Patent No.: US 12,216,109 B2
(45) Date of Patent: Feb. 4, 2025

(54) BIOSENSOR, BIOSENSOR ARRAY AND DEVICE

(71) Applicant: Samsung Electronics Co., Ltd., Suwon-si (KR)

(72) Inventors: Hyun Bum Kang, Yongin-si (KR); Gae Hwang Lee, Seongnam-si (KR); Jong Won Chung, Hwaseong-si (KR); Joo Young Kim, Hwaseong-si (KR); Youngjun Yun, Seongnam-si (KR); Suk Gyu Hahm, Gyungju-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 811 days.

(21) Appl. No.: 17/388,630

(22) Filed: Jul. 29, 2021

(65) Prior Publication Data
US 2022/0042965 A1    Feb. 10, 2022

(30) Foreign Application Priority Data
Aug. 5, 2020    (KR) .................. 10-2020-0098177

(51) Int. Cl.
*G01N 33/48*    (2006.01)
*H01L 27/146*    (2006.01)
*H05K 1/02*    (2006.01)
*H10K 59/122*    (2023.01)

(52) U.S. Cl.
CPC ....... *G01N 33/48* (2013.01); *H01L 27/14609* (2013.01); *H05K 1/0283* (2013.01); *H10K 59/122* (2023.02)

(58) Field of Classification Search
CPC .. G01N 33/48; H01L 27/14609; H10K 59/60; H10K 59/122; H10K 65/00; H10K 77/111
USPC .......................................................... 257/40
See application file for complete search history.

(56) References Cited

U.S. PATENT DOCUMENTS

| | | | |
|---|---|---|---|
| 9,853,246 B2 | 12/2017 | Kwon | |
| 10,510,778 B2 | 12/2019 | Li | |
| 10,892,314 B2 | 1/2021 | Kim et al. | |
| 2018/0114947 A1 | 4/2018 | Kwon | |
| 2019/0133470 A1 | 5/2019 | Szabados | |
| 2020/0006684 A1 | 1/2020 | Liu et al. | |
| 2021/0026497 A1* | 1/2021 | Lee | G06F 3/0448 |
| 2021/0050404 A1 | 2/2021 | Kim et al. | |
| 2021/0296599 A1* | 9/2021 | Kim | H10K 59/122 |
| 2022/0030705 A1* | 1/2022 | Lee | H05K 1/0277 |

FOREIGN PATENT DOCUMENTS

| | | | | |
|---|---|---|---|---|
| CN | 111179754 A | * | 5/2020 | ............. G09F 9/301 |
| KR | 2016-0088522 A | | 7/2016 | |
| KR | 2020-0009921 A | | 1/2020 | |

* cited by examiner

*Primary Examiner* — Fazli Erdem
(74) *Attorney, Agent, or Firm* — Harness, Dickey & Pierce, P.L.C.

(57) ABSTRACT

A biosensor includes a stretchable substrate, a pixel defining layer on the stretchable substrate and including a first pixel defining layer at least partially defining a first opening and a second pixel defining layer at least partially defining a second opening, a photo-detecting element at least partially in the first opening, and a first light emitting element at least partially in the second opening, wherein an area of the first pixel defining layer is equal to or greater than about twice an area of the first opening.

21 Claims, 15 Drawing Sheets

BIOSENSOR, BIOSENSOR ARRAY AND DEVICE

CROSS-REFERENCE TO RELATED APPLICATION

This application claims priority to and the benefit of, under 35 U.S.C. § 119, Korean Patent Application No. 10-2020-0098177 filed in the Korean Intellectual Property Office on Aug. 5, 2020, the entire contents of which are incorporated herein by reference.

BACKGROUND

1. Field

A biosensor, a biosensor array, and a device are disclosed.

2. Description of the Related Art

Recently, research on attachable devices directly attaching display devices or biological devices such as smart skin devices, soft robots, and biomedical devices to skin or clothing has been conducted.

However, such an attachable device is required to have stretchability in an arbitrary direction to flexibly respond to motions of a living body, and simultaneously, to recover to its original state.

SUMMARY

Some example embodiments provide a biosensor capable of reducing or preventing deterioration of device performance during a process.

Some example embodiments provide a biosensor array including the biosensor.

Some example embodiments provide a device including the biosensor array.

According to some example embodiments, a biosensor may include a stretchable substrate, a pixel defining layer on the stretchable substrate, the pixel defining layer including a first pixel defining layer defining a first opening extending through a thickness of the first pixel defining layer, and a second pixel defining layer defining a second opening extending through a thickness of the second pixel defining layer, a photo-detecting element at least partially in the first opening, and a first light emitting element at least partially in the second opening. An area of the first pixel defining layer may be equal to or greater than about twice an area of the first opening.

The area of the first pixel defining layer may be about 2.4 times to about 25 times the area of the first opening.

The area of the first pixel defining layer excluding the first opening may be greater than the area of the first opening.

The area of the first pixel defining layer excluding the first opening may be about 1.1 times to about 24 times the area of the first opening.

The first pixel defining layer excluding the first opening may be in direct contact with the stretchable substrate.

An area of the second pixel defining layer may be equal to or greater than about twice an area of the second opening.

An area of the second pixel defining layer excluding the second opening may be greater than an area of the second opening.

The second pixel defining layer excluding the second opening may be in direct contact with the stretchable substrate.

The first pixel defining layer and the second pixel defining layer may be connected, and a boundary between the first pixel defining layer and the second pixel defining layer may be located halfway along a gap between an edge of the first opening and an edge of the second opening facing each other.

A magnitude of the gap between the edge of the first opening and the edge of the second opening facing each other may be about 0.4 times to about 4 times a magnitude of a width of the first opening or a width of the second opening in a direction extending parallel to a direction of the gap.

The area of the pixel defining layer may be equal to or greater than about twice a sum of the area of the first opening and an area of the second opening.

The photo-detecting element may include a first electrode and a second electrode facing each other, and a photoelectric conversion layer between the first electrode and the second electrode, wherein an area of an active region of the photo-detecting element may be substantially equal to the area of the first opening.

The first light emitting element may include a third electrode and a fourth electrode facing each other, and a light emitting layer between the third electrode and the fourth electrode, wherein a light emitting area of the first light emitting element may be substantially equal to an area of the second opening.

The first pixel defining layer and the second pixel defining layer may be isolated from direct contact with each other.

The pixel defining layer may further include a third pixel defining layer at least partially defining a third opening extending through a thickness of the third pixel defining layer, and the biosensor may further include a second light emitting element at least partially in the third opening.

An area of the third pixel defining layer may be equal to or greater than about twice an area of the third opening.

The second light emitting element may be configured to emit light of different wavelength spectra from the first light emitting element.

The stretchable substrate may include a plurality of first regions and a second region between adjacent first regions of the plurality of first regions, the first regions having a first stiffness and the second region having a second stiffness that is lower than the first stiffness and the photo-detecting element and the first light emitting element may be on separate, respective first regions of the plurality of first regions.

The biosensor may be a skin-attachable patch typed biosensor or a skin-attachable band typed biosensor.

Some example embodiments provide a biosensor array including the biosensor.

Some example embodiments provide a device including the biosensor array.

A biosensor capable of reducing or preventing deterioration of device performance during processing may be provided.

DETAILED DESCRIPTION

Figure 1:
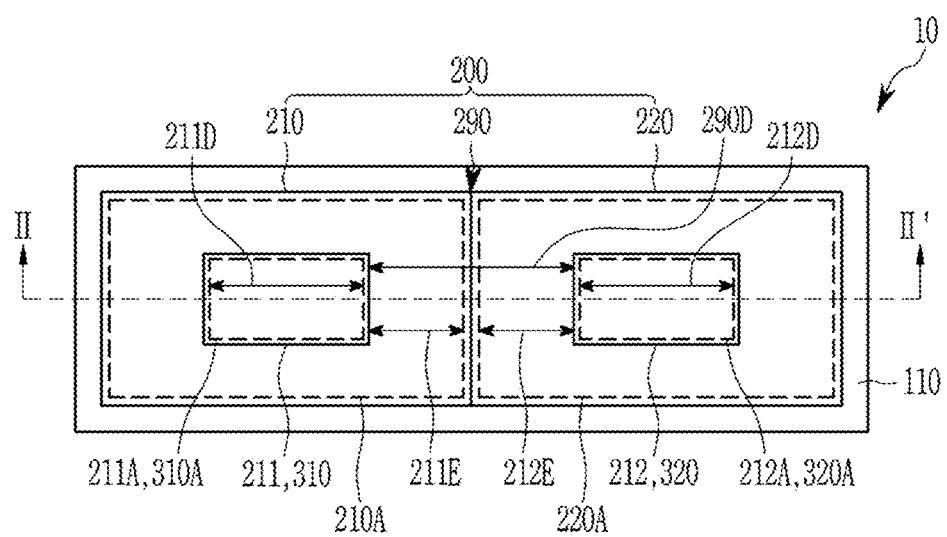
FIG. 1 is a vertical plan view of an upper portion of a biosensor according to some example embodiments.

Hereinafter, some example embodiments are described in detail so that those skilled in the art can easily implement them. However, the actual applied structure may be implemented in various different forms and is not limited to the implementations described herein.

In the drawings, the thickness of layers, films, panels, regions, etc., are exaggerated for clarity. It will be understood that when an element such as a layer, film, region, or substrate is referred to as being "on" another element, it may be directly on the other element or intervening elements may also be present. In contrast, when an element is referred to as being "directly on" another element, there are no intervening elements present.

Hereinafter, the term "combination" includes a mixture and two or more stacked structures.

It will be understood that elements and/or properties thereof (e.g., structures, surfaces, directions, or the like), which may be referred to as being "perpendicular," "parallel," "coplanar," or the like with regard to other elements and/or properties thereof (e.g., structures, surfaces, directions, or the like) may be "perpendicular," "parallel," "coplanar," or the like or may be "substantially perpendicular," "substantially parallel," "substantially coplanar," respectively, with regard to the other elements and/or properties thereof.

Elements and/or properties thereof (e.g., structures, surfaces, directions, or the like) that are "substantially perpendicular" with regard to other elements and/or properties thereof will be understood to be "perpendicular" with regard to the other elements and/or properties thereof within manufacturing tolerances and/or material tolerances and/or have a deviation in magnitude and/or angle from "perpendicular," or the like with regard to the other elements and/or properties thereof that is equal to or less than 10% (e.g., a. tolerance of ±10%)).

Elements and/or properties thereof (e.g., structures, surfaces, directions, or the like) that are "substantially parallel" with regard to other elements and/or properties thereof will be understood to be "parallel" with regard to the other elements and/or properties thereof within manufacturing tolerances and/or material tolerances and/or have a deviation in magnitude and/or angle from "parallel," or the like with regard to the other elements and/or properties thereof that is equal to or less than 10% (e.g., a. tolerance of ±10%)).

Elements and/or properties thereof (e.g., structures, surfaces, directions, or the like) that are "substantially coplanar" with regard to other elements and/or properties thereof will be understood to be "coplanar" with regard to the other elements and/or properties thereof within manufacturing tolerances and/or material tolerances and/or have a deviation in magnitude and/or angle from "coplanar," or the like with regard to the other elements and/or properties thereof that is equal to or less than 10% (e.g., a. tolerance of ±10%)).

It will be understood that elements and/or properties thereof may be recited herein as being "the same" or "equal" as other elements, and it will be further understood that elements and/or properties thereof recited herein as being "the same" as or "equal" to other elements may be "the same" as or "equal" to or "substantially the same" as or "substantially equal" to the other elements and/or properties thereof. Elements and/or properties thereof that are "substantially the same" as or "substantially equal" to other elements and/or properties thereof will be understood to include elements and/or properties thereof that are the same as or equal to the other elements and/or properties thereof within manufacturing tolerances and/or material tolerances. Elements and/or properties thereof that are the same or substantially the same as other elements and/or properties thereof may be structurally the same or substantially the same, functionally the same or substantially the same, and/or compositionally the same or substantially the same.

It will be understood that elements and/or properties thereof described herein as being the "substantially" the same encompasses elements and/or properties thereof that have a relative difference in magnitude that is equal to or less than 10%. Further, regardless of whether elements and/or properties thereof are modified as "substantially," it will be understood that these elements and/or properties thereof should be construed as including a manufacturing or operational tolerance (e.g., ±10%) around the stated elements and/or properties thereof.

When the terms "about" or "substantially" are used in this specification in connection with a numerical value, it is intended that the associated numerical value include a tolerance of ±10% around the stated numerical value. When ranges are specified, the range includes all values therebetween such as increments of 0.1%.

Hereinafter, a biosensor according to some example embodiments is described with reference to the drawings.

Figure 2:
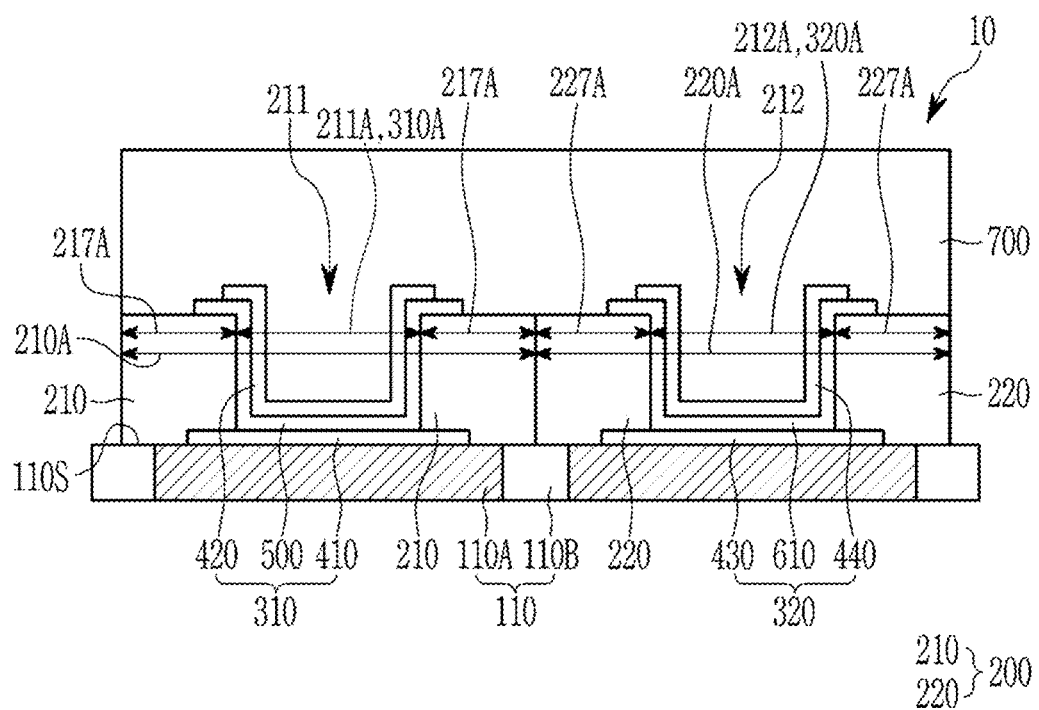
FIG. 2 is a cross-sectional view of the biosensor of FIG. 1 taken along line II-II'.

FIG. 1 is a plan view showing an example of a biosensor according to some example embodiments, and FIG. 2 is a cross-sectional view of the biosensor of FIG. 1 taken along line II-II'.

Referring to FIGS. 1 and 2, a biosensor 10 according to some example embodiments include a stretchable substrate 110, a photo-detecting element 310, a first light emitting element 320, and a pixel defining layer (PDL) 200.

The stretchable substrate 110 may flexibly respond to external forces or external motions such as twisting, pressing, and pulling due to relatively low stiffness and high elongation rate, and may be easily restored to the original state.

The stretchable substrate 110 may include an elastomer. The elastomer may include an organic elastomer, an organic-inorganic elastomer, an inorganic elastomer-like material, or a combination thereof. The organic elastomer or the organic-inorganic elastomer may be, for example, a substituted or unsubstituted polyorganosiloxane such as polydimethylsiloxane (PDMS); an elastomer including a substituted or unsubstituted butadiene moiety such as styrene-ethylene-butylene-styrene (SEBS); a polyethylene-based elastomer such as polyethylene terephthalate or polyethylene naphthalate; a polyimide-based elastomer; an elastomer including a urethane moiety; an elastomer including an acrylic moiety; an elastomer including an olefin moiety; or a combination thereof, but is not limited thereto. The inorganic elastomer-like material may include an elastic ceramic, a solid metal, a liquid metal, or a combination thereof, but is not limited thereto.

The stretchable substrate 110 may include regions having different stiffness, for example, a first region 110A having relatively high "first" stiffness and a second region 110B having a relatively lower "second" stiffness than the first region 110A. Herein, the stiffness indicates a degree of resistance to deformation when a force is applied from the outside. Relatively high stiffness means that the resistance to deformation is relatively large, so that deformation is small while relatively low stiffness means that the resistance to deformation is relatively small, so that the deformation is large.

The stiffness may be evaluated from an elastic modulus, and a high elastic modulus may mean high stiffness and a low elastic modulus may mean low stiffness. The elastic modulus may be, for example, a Young's modulus. A difference between elastic moduli of the first region 110A and the second region 110B of the stretchable substrate 110 may be about 100 times or more, and the elastic modulus of the first region 110A may be about 100 times higher than the elastic modulus of the second region 110B. The difference between the elastic modulus of the first region 110A and the second region 110B may be about 100 to 100,000 times within the above range, and the elastic modulus of the first region 110A may be about 100 times to about 100,000 times higher than the elastic modulus of the second region 110B, but is not limited thereto. For example, the elastic modulus of the first region 110A may be about $10^7$ Pa to about $10^{12}$ Pa, and the elastic modulus of the second region 110B may be greater than or equal to about $10^2$ Pa and less than about $10^7$ Pa, but is not limited thereto. For example, the first region 110A, having a first stiffness that is greater than a second stiffness of the second region 110B, may have a first elastic modulus that is greater than the elastic modulus of the second region 110B (e.g., second elastic modulus).

Elongation rates of the first region 110A and the second region 110B of the stretchable substrate 110 may be different due to the aforementioned difference in stiffness, and the elongation rate of the second region 110B may be higher than the elongation rate of the first region 110A. Herein, the elongation rate may be a percentage of the length change that is increased to a breaking point with respect to the initial length. For example, the elongation rate of the first region 110A of the stretchable substrate 110 may be less than or equal to about 5%, within the range, about 0% to about 5%, about 0% to about 4%, about 0% to about 3%, about 0% to about 2%, about 0% to about 1%, about 0.5% to about 5%, about 0.5% to about 4%, about 0.5% to about 3%, about 0.5% to about 2%, or about 1% to about 2%. For example, the elongation rate of the second region 110B of the stretchable substrate 110 may be greater than or equal to about 10%, within the range, about 10% to about 300%, about 10% to about 200%, about 10% to about 100%, about 10% to about 90%, about 10% to about 80%, about 10% to about 70%, about 10% to about 60%, about 10% to about 50%, about 10% to about 40%, about 20% to about 70%, about 20% to about 60%, about 20% to about 50%, or about 20% to about 40%.

The adjacent first regions 110A of the stretchable substrate 110 may have island shapes separated from (e.g., isolated from direct contact with) each other, and a photo-detecting element 310 and the first light emitting element 320 to be described later may be disposed in the first region 110A of the stretchable substrate 110. For example, as shown in FIGS. 1-2, the stretchable substrate 110 may include a plurality of first regions 110A and a second region 110B between adjacent first regions 110A of the plurality of first regions 110A, the first regions 110A having a first stiffness and the second region 110B having a second stiffness that is lower than the first stiffness, and where the photo-detecting element 310 and the first light emitting element 320 are on separate, respective first regions 110A of the plurality of first regions 110A of the stretchable substrate 110.

The second region 110B of the stretchable substrate 110 may be a region other than the plurality of first regions 110A, and may be continuously connected entirely. The second region 110B of the stretchable substrate 110 may be a region providing stretchability. Due to its relatively low stiffness and high elongation rate, the second region 110B may flexibly respond to external forces or external motions such as twisting and pulling, and may be easily restored to its original state.

For example, the first region 110A and the second region 110B of the stretchable substrate 110 may have different shapes. For example, the first region 110A of the stretchable substrate 110 may be flat and the second region 110B may include a two-dimensional or three-dimensional stretchable structure. The two-dimensional or three-dimensional stretchable structure may have, for example, a wavy shape, a wrinkle shape, a pop-up shape, or a non-coplanar mesh shape, but is not limited thereto.

For example, the first region 110A and the second region 110B of the stretchable substrate 110 may include different materials. For example, the first region 110A of the stretchable substrate 110 may include an inorganic material, an organic material and/or an organic/inorganic material having relatively high stiffness and a low elongation rate, and the second region 110B of the stretchable substrate 110 may include an inorganic material, an organic material and/or an organic/inorganic material having a relatively low stiffness and high elongation rate. For example, the first region 110A of the stretchable substrate 110 may include an organic material such as polycarbonate, polymethylmethacrylate, polyethyleneterephthalate, polyethylenenaphthalate, polyimide, polyamide, polyamideimide, polyethersulfone, or a combination thereof, a carbon structure such as diamond carbon and the second region 110B of the stretchable substrate 110 may include an organic or organic/inorganic elastomer such as a substituted or unsubstituted polyorganosiloxane such as polydimethylsiloxane, an elastomer including a substituted or unsubstituted butadiene moiety such as styrene-ethylene-butylene-styrene, an elastomer including a urethane moiety, an elastomer including an acrylic moiety, an elastomer including an olefin moiety, or a combination thereof; an inorganic elastomer-like material such as ceramic, a solid metal, a liquid metal, or a combination thereof, but they are not limited thereto.

For example, the first region 110A and the second region 110B of the stretchable substrate 110 may be formed with (e.g., at least partially comprise) the same material, and may have different stiffness by different conditions such as polymerization degrees and/or curing degrees. For example, the stretchable substrate 110 may have the first region 110A having a relatively high stiffness and the second region 110B having a relatively low stiffness which are formed by varying the polymerization degrees, types and contents of curing agents, and/or curing temperatures, based on polydimethylsiloxane.

In this way, the stretchable substrate 110 includes the first region 110A having relatively high stiffness and a low elongation rate and the second region 110B having relatively low stiffness and a high elongation rate, and the photo-detecting element 310 and the first light emitting element 320 are disposed in the first region 110A, and thereby when a large external force or motion is applied to the stretchable substrate 110, the photo-detecting element 310 and the first light emitting element 320 in the first region 110A receives relatively smaller strain, and thus may be at least partially protected from, or prevented from, being damaged or destroyed due to the extreme strain.

A photo-detecting element 310 and a first light emitting element 320 are disposed on the stretchable substrate 110. The photo-detecting element 310 and the first light emitting element 320 are separated (e.g., isolated from direct contact with each other) by a particular (or, alternatively, predetermined) interval.

The photo-detecting element 310 may include a first electrode 410 and a second electrode 420 facing each other, and a photoelectric conversion layer 500 between the first electrode 410 and the second electrode 420, wherein the area 310A of an active region of the photo-detecting element 310 (e.g., the active region of the photo-detecting element 310 may be defined as a region where the first and second electrodes 410 and 420 and the photoelectric conversion layer 500 overlap in the vertical direction perpendicular to the upper surface 110S) may be substantially equal to the area 211A of the first opening 211, where "area" refers to an area in a plane that is parallel to the in-plane direction of the stretchable substrate 110 (e.g., a plane that is parallel to the upper surface 110S of the stretchable substrate 110). As shown in FIG. 2, the photo-detecting element 310 may be at least partially in the first opening 211 based on a first electrode 410, second electrode 420, and photoelectric conversion layer 500 at least partially covering one or more surfaces of the first opening 211, which may include the upper surface 110S of the stretchable substrate 110 that is exposed by the first opening 211 and/or one or more inner surfaces of the first pixel defining layer 210 that at least partially define the first opening 211.

The photo-detecting element 310 is configured to convert an optical signal (e.g., incident light) into an electrical signal.

The photoelectric conversion layer 500 may be configured to absorb light of at least a portion of a visible light wavelength spectrum, for example, and absorb light of at least one of a blue wavelength spectrum, a green wavelength spectrum, or a red wavelength spectrum. The blue wavelength spectrum may, for example, have a maximum absorption wavelength ($\lambda_{max}$) at greater than or equal to about 400 nm and less than about 500 nm, the green wavelength spectrum may have a maximum absorption wavelength ($\lambda_{max}$) at about 500 nm to about 600 nm, and the red wavelength spectrum may have a maximum absorption wavelength ($\lambda_{max}$) at greater than about 600 nm and less than or equal to about 700 nm. As an example, the photoelectric conversion layer 500 may be configured to absorb light of the blue wavelength spectrum, the green wavelength spectrum, and the red wavelength spectrum, that is, the light of an entire visible wavelength spectrum, for example, may be configured to absorb white light. The photoelectric conversion layer 500 configured to absorb white light may be formed by blending, for example, a blue light absorbing material, a green light absorbing material, and a red light absorbing material, or by stacking a blue light absorbing layer, a green light absorbing layer, and a red light absorbing layer.

The photoelectric conversion layer 500 may include an organic light absorbing material, an inorganic light absorbing material, and/or an organic/inorganic light absorbing material. The organic light absorbing material may be a low molecular weight light absorbing material and/or a polymer light absorbing material and the inorganic light absorbing material may be a semiconductor compound, a quantum dot, and/or a perovskite, but they are not limited thereto.

One of the first electrode 410 or the second electrode 420 may be an anode and the other may be a cathode. For example, the first electrode 410 may be an anode and the second electrode 420 may be a cathode. For example, the first electrode 410 may be a cathode and the second electrode 420 may be an anode.

The first electrode 410 may be a reflective electrode and the second electrode 420 may be a transflective electrode. The reflective electrode may be made of, for example, an opaque conductor or may include a reflective layer including an opaque conductor. The reflective electrode may have a light transmittance of less than about 10%, for example, a light transmittance of less than or equal to about 8%, less than or equal to about 7%, less than or equal to about 5%, less than or equal to about 3%, or less than or equal to about 1%, and the light transmittance may be equal to or greater than about 0%, 0.1%, 0.5%, or the like. The reflective electrode has a reflectance of greater than or equal to about 10%, and may have a reflectance of, for example, greater than or equal to about 20%, greater than or equal to about 30%, greater than or equal to about 50%, or greater than or equal to about 70%, and the reflectance may be equal to or less than about 100%, 99.9%, 99.5%, or the like. The transflective electrode may have light transmittance between the transparent electrode and the reflective electrode, and may have a light transmittance of about 10% to about 70%, about 20% to about 60%, or about 30% to about 50%.

At least one of the first electrode 410 or the second electrode 420 may be a stretchable electrode. For example, each of the first electrode 410 and the second electrode 420 may be a stretchable electrode.

The stretchable electrode may include, for example, a stretchable conductor or may be formed into a stretchable shape. The stretchable conductor may include, for example, a liquid metal, a conductive nanostructure, or a combination thereof.

The liquid metal may be an alloy composed of a plurality of metals and/or semi-metals, and may exist in a liquid state at room temperature (about 25° C.). The liquid metal may be an alloy including at least one selected from, for example, copper (Cu), titanium (Ti), nickel (Ni), zirconium (Zr), iron (Fe), magnesium (Mg), calcium (Ca), cobalt (Co), palladium (Pd), platinum (Pt), gold (Au), cerium (Ce), lanthanum (La), yttrium (Y), gadolinium (Gd), beryllium (Be), tantalum (Ta), gallium (Ga), indium (In), aluminum (Al), hafnium (Hf), niobium (Nb), lead (Pb), platinum (Pt), silver (Ag), phosphorus (P), boron (B), silicon (Si), carbon (C), tin (Sn), molybdenum (Mo), tungsten (W), zinc (Zn), manganese (Mn), erbium (Er), chromium (Cr), praseodymium (Pr), thulium (Tm), and/or a combination thereof, but is not limited thereto.

The conductive nanostructure may include, for example, a conductive nanoparticle, a conductive nanoflake, a conductive nanowire, a conductive nanotube, or a combination thereof, for example a nanoparticle, a nanoflake, nanowire, a nanotube or a combination thereof including a low-resistance conductor such as silver, gold, copper, aluminum, and the like or a carbon conductor, and for example a silver nanoparticle, a silver nanoflake, a silver nanowire, a silver nanotube, a carbon nanotube, graphene, graphite, or a combination thereof, but is not limited thereto.

The stretchable shape may be, for example, a wavy shape, a wrinkle shape, a popup shape, or a non-coplanar mesh shape, but is not limited thereto.

For example, each of the first electrode 410 and the second electrode 420 may be a stretchable electrode including a liquid metal, wherein the first electrode 410, which is a reflective electrode, may have a sufficient thickness of greater than or equal to about 80 nm and the second electrode 420, which is a transflective electrode, may have a thickness thinner than that of the reflective electrode, and may have, for example, a thickness of about 5 nm to about 50 nm.

The first light emitting element 320 includes a third electrode 430 and a fourth electrode 440 facing each other, and a first light emitting layer 610 between the third electrode 430 and the fourth electrode 440, and the area 320A of the active region (e.g., light emitting area) of the first light emitting element 320 (e.g., the active region of the photo-detecting element 310 and/or light emitting area thereof may be defined as a region where the third and fourth electrodes 430 and 440 and the first light emitting layer 610 overlap in the vertical direction perpendicular to the upper surface 110S) may be substantially equal to the area 212A of the second opening 212, where "area" refers to an area in a plane that is parallel to the in-plane direction of the stretchable substrate 110 (e.g., a plane that is parallel to the upper surface 110S of the stretchable substrate 110). As shown in FIG. 2, the first light emitting element 320 may be at least partially in the second opening 212 based on the third electrode 430, fourth electrode 440, and first light emitting layer 610 at least partially covering one or more surfaces of the second opening 212, which may include the upper surface 110S of the stretchable substrate 110 that is exposed by the second opening 212 and/or one or more inner surfaces of the second pixel defining layer 220 that at least partially define the second opening 212.

The first light emitting element 320 may be configured to convert an electrical signal into an optical signal (e.g., emitted light), and may be, for example, a light emitting diode, and the light emitting diode may be, for example, an organic light emitting diode, a quantum dot light emitting diode, or a perovskite light emitting diode.

The first light emitting layer 610 may be configured to emit light of, for example, at least a portion of a visible light wavelength spectrum, for example, and may be configured to emit light of at least one of a blue wavelength spectrum, a green wavelength spectrum, or a red wavelength spectrum. The blue wavelength spectrum may, for example, have a maximum emission wavelength ($\lambda_{max}$) at greater than or equal to about 400 nm and less than about 500 nm, the green wavelength spectrum may have a maximum emission wavelength ($\lambda_{max}$) at about 500 nm to about 600 nm, and the red wavelength spectrum may have be a maximum emission wavelength ($\lambda_{max}$) at greater than about 600 nm and less than or equal to about 700 nm. As an example, the first light emitting layer 610 may be configured to emit light of the blue wavelength spectrum, the green wavelength spectrum, and the blue wavelength spectrum, that is, the light of an entire visible wavelength spectrum, for example, may be configured to emit white light. The first light emitting layer 610 configured to emit white light may be formed by blending, for example, a blue light emitting material, a green light emitting material, and a red light emitting material, or may be formed by stacking a blue light emitting layer, a green light emitting layer, and a red light emitting layer.

The first light emitting layer 610 may include an organic light emitting material, an inorganic light emitting material, and/or an organic/inorganic light emitting material. The organic light emitting material may be a low molecular light emitting material and/or a polymer light emitting material, and the inorganic light emitting material may be a semiconductor compound, a quantum dot, and/or perovskite, but are not limited thereto.

The third electrode 430 and the fourth electrode 440 may be the same as the first electrode 410 and the second electrode 420 described above.

The pixel defining layer 200 is formed on (e.g., directly or indirectly on) the stretchable substrate 110, and may define a region of the photo-detecting element 310 and a region of the first light emitting element 320, respectively. The pixel defining layer 200 may include a first pixel defining layer 210 for defining the region of the photo-detecting element 310 and a second pixel defining layer 220 for defining the region of the first light emitting element 320, and the first pixel defining layer 210 may have (e.g., include one or more inner surfaces that at least partially define) a first opening 211 where the photo-detecting element 310 is disposed, and the second pixel defining layer 220 may have (e.g., include one or more inner surfaces that at least partially define) a second opening 212 where the first light emitting element 320 is disposed. As shown, the first opening 211 may be at least partially defined by one or more inner surfaces of the first pixel defining layer 210 and may be further defined by a portion of the upper surface 110S of the stretchable substrate 110 that is exposed by the first opening 211 (e.g., a portion of an upper surface of the first region 110A of the stretchable substrate 110). As shown, the second opening 212 may be at least partially defined by one or more inner surfaces of the second pixel defining layer 220 and may be further defined by a portion of the upper surface 110S of the stretchable substrate 110 that is exposed by the second opening 212 (e.g., a portion of an upper surface of a separate first region 110A of the stretchable substrate 110). As shown, the first and second openings 211 and 212 extend through the respective thicknesses of the first and second pixel defining layers 210 and 220 in a vertical direction that extends perpendicular to the upper surface 110S of the stretchable substrate 110 (e.g., perpendicular to the in-plane direction of the stretchable substrate 110).

As shown, the photo-detecting element 310 may be at least partially located within the first opening 211, where portions of the photo-detecting element 310 may or may not extend, in a direction parallel to the upper surface 110S, beyond the boundaries of the first opening 211. For example, as shown in FIG. 2, portions of the first and second electrodes 410 and 420 and the photoelectric conversion layer 500 may extend in the direction parallel to the upper surface 110S beyond the lateral boundaries of the first opening 211 as at least partially defined by one or more inner surfaces of the first pixel defining layer 210. However, example embodiments are not limited thereto, and in some example embodiments the first and second electrodes 410 and 420 and the photoelectric conversion layer 500 may be entirely located within the first opening 211 and may not extend beyond the first opening 211 in the direction parallel to the upper surface 110S.

As shown, first light emitting element 320 may be at least partially located within the second opening 212, where portions of the first light emitting element 320 may or may not extend, in a direction parallel to the upper surface 110S, beyond the boundaries of the second opening 212. For example, as shown in FIG. 2, portions of the third and fourth electrodes 430 and 440 and the first light emitting layer 610 may extend in the direction parallel to the upper surface 110S beyond the lateral boundaries of the first opening 212 as at least partially defined by one or more inner surfaces of the second pixel defining layer 220. However, example embodiments are not limited thereto, and in some example embodiments the third and fourth electrodes 430 and 440 and the first light emitting layer 610 may be entirely located within the second opening 212 and may not extend beyond the second opening 212 in the direction parallel to the upper surface 110S.

As shown in FIGS. 1-2, the first pixel defining layer 210 and the second pixel defining layer 220 may be disposed in parallel along the in-plane direction of the stretchable substrate 110 (where the in-plane direction of the stretchable substrate 110 may be parallel to the upper surface 110S of the stretchable substrate 110), and may be, for example, continuously and adjacently disposed. The boundary of the first pixel defining layer 210 and the second pixel defining layer 220 may be between the first opening 211 and the second opening 212, and may be, for example, a half point of the gap between the edge of the first opening 211 and the edge of the second opening 212 facing each other. For example, as shown in FIG. 1, the boundary 290 (e.g., interface) between the first and second pixel defining layers 210 and 220 that are directly connected to each other (e.g., in direct contact with each other) may be located a distance 211E in the in-plane direction of the stretchable substrate 110 (e.g., parallel to the upper surface 110S) from a proximate edge of the first opening 211 and may be located a distance 212E in the in-plane direction of the stretchable substrate 110 (e.g., parallel to the upper surface 110S) from a proximate edge of the second opening 212, where distances 211E and 212E may be equal to each other, and where the distances 211E and 212E may be one half the distance 290D (e.g., gap) in the in-plane direction of the stretchable substrate 110 (e.g., parallel to the upper surface 110S) between respective edges of the first and second opening 211 and 212 facing each other. Accordingly, the boundary 290 may be located halfway along the gap (e.g., distance 290D). In some example embodiments, a magnitude of the gap (e.g., distance 290D) between the edge of the first opening 211 and the edge of the second opening 212 facing each other may be about 0.4 times to about 4 times of a magnitude of the width 211D of the first opening 211 (e.g., distance between opposing edges of the first opening 211 in the direction parallel to the direction of distance 290D) or a magnitude of the width 212D of the second opening 212 (e.g., distance between opposing edges of the second opening 212 in the direction parallel to the direction of distance 290D).

In general, in order to realize high-performance biosensor signal characteristics with a signal to noise ratio (SNR) of greater than or equal to about 15 dB, it is necessary to maintain a gap between the photo-detecting element 310 and the first light emitting element 320 in an appropriate range. The gap between the edge of the first opening 211 and the edge of the second opening 212 which include the photo-detecting element 310 and the first light emitting element 320, respectively is set to an appropriate range (optimum distance). If the gap is too narrow or wide, the signal sensitivity characteristics may be deteriorated. As described above, when the gap between the edge of the first opening 211 and the edge of the second opening 212 is about 0.4 times to about 4 times, for example, about 0.6 times to about 4 times, about 0.8 times to about 4 times, about 1.0 times to about 4 times, about 0.4 times to about 3.8 times, about 0.4 times to about 3.6 times, about 0.4 times to about 3.4 times, about 0.4 times to about 3.2 times, or about 0.4 times to about 3.0 times the width of the first opening 211 or the second opening 212, a biosensor having excellent signal sensitivity may be implemented.

The pixel defining layer 200 may include an organic material, an inorganic material, and/or an organic-inorganic material, and may include, for example, a photosensitive organic polymer. The photosensitive organic polymer may include, for example, polymethyl methacrylate (PMMA), polyimide (PI), and the like, but is not limited thereto. The pixel defining layer may be formed through, for example, photolithography, and accordingly the area 210A of the first pixel defining layer 210, the area 220A of the second pixel defining layer 220, the area 211A of the first opening 211 and/or the area 212A of the second opening 212 may be effectively adjusted. In addition, the distance between the photo-detecting element 310 and the first light emitting element 320 may be controlled by adjusting the area of the pixel defining layer when forming the biosensor, so that the signal sensitivity of the biosensor may be improved.

The pixel defining layer 200 may be in contact (e.g., direct contact) with the stretchable substrate 110, and may be, for example, in contact with the whole region excluding portions of contacting the first electrode 410 of the photo-detecting element 310 and the third electrode 430 of the first light emitting element 320. As shown in FIG. 2, for example, a portion (e.g., some or all) of the first pixel defining layer 210 excluding the first opening 211 may be in direct contact with the stretchable substrate 110. In FIG. 2, a portion of the first pixel defining layer 210 excluding the first opening 211 may be isolated from direct contact with the stretchable substrate 110 by a portion of the first electrode 410, but in some example embodiments, all of the first pixel defining layer 210 excluding the first opening 211 may be in direct contact with the stretchable substrate 110. As shown in FIG. 2, for example, a portion (e.g., some or all) of the second pixel defining layer 220 excluding the second opening 212 may be in direct contact with the stretchable substrate 110. In FIG. 2, a portion of the second pixel defining layer 220 excluding the second opening 212 may be isolated from direct contact with the stretchable substrate 110 by a portion of the third electrode 430, but in some example embodiments, all of the second pixel defining layer 220 excluding the second opening 212 may be in direct contact with the stretchable substrate 110.

The pixel defining layer 200 may be formed in a sufficiently wide area (e.g., area of sufficiently great magnitude) on the stretchable substrate 110, and accordingly the pixel defining layer 200 is at least partially protected from, or prevented from, being lifted or delaminated from the stretchable substrate 110.

One example method of manufacturing elements including the aforementioned stretchable substrate 110 may include forming a flexible stretchable substrate 110 on a rigid support substrate such as a glass substrate in terms of ease and stability of the process; forming a pixel defining layer 200, a photo-detecting element 310, and a first light emitting element 320 on the stretchable substrate 110; and separating the stretchable substrate 110 from the support substrate through a wet process. The wet process may be, for example, a method of weakening adherence between the support substrate and the stretchable substrate 110 to separate the stretchable substrate 110 from the support substrate by, for example, dipping the support substrate formed with the elements into liquid such as water or supplying liquid such as water by a method of spraying or coating to remove a sacrificial layer between the support substrate and the stretchable substrate 110.

When the stretchable substrate 110 is separated through the wet process, the elements may be applied with the particular (or, alternatively, predetermined) strain stress during separating the stretchable substrate 110 from the support substrate, and thus the elements may be lifted and/or delaminated from the stretchable substrate 110 by the strain stress, or the performance of the element may be deteriorated. But in a case of the biosensor 10 according to some example embodiments, the pixel defining layer 200 on the stretchable substrate 110 is formed in a sufficiently wide (e.g., sufficiently great) area, so that the stability of the elements on the stretchable substrate 110 may be enhanced during the separating the stretchable substrate 110 from the support substrate, thereby the strain stress applied to the elements may be reduced or removed, and the elements may be at least partially protected from, or prevented from, being lifted and/or delaminated, and so resultantly, the deterioration of performance of the biosensor 10 may be reduced or prevented.

In order to effectively reduce or reduce or prevent the lifting and/or delaminating the element during the process, some example embodiments may provide sufficient area of the pixel defining layer on the stretchable substrate 110, for example, may provide the pixel defining layer with the sufficiently wider (e.g., greater) area than the area of the first and second openings 211 and 212.

The area 210A of the first pixel defining layer 210 may be, for example, about twice or more (e.g., equal to or greater than about 2 times), for example, about 2.4 times or more, about 2.5 times or more, about 3 times or more, about 4 times or more, about 5 times or more, about 6 times or more, about 7 times or more, about 8 times or more, about 9 times or more, or about 10 times or more, for example about 2.4 times to about 25 times, about 2.4 times to about 24 times, about 2.4 times to about 23 times, about 2.4 times to about 22 times, about 2.4 times to about 21 times, about 2.4 times to about 20 times, about 2.4 times to about 19 times, about 2.4 times to about 18 times, about 2.4 times to about 17 times, about 2.4 times to about 16 times, about 2.4 times to about 15 times, about 2.5 times to about 25 times, about 3 times to about 25 times, about 4 times to about 25 times, about 5 times to about 25 times, about 6 times to about 25 times, about 7 times to about 25 times, about 8 times to about 25 times, about 9 times to about 25 times, about 10 times to about 25 times wider (e.g., greater) than the area 211A of the first opening 211, but the present inventive concepts are not limited thereto.

In some example embodiments, and as shown in at least FIGS. 1-2, the area 210A of the first pixel defining layer 210 means an area including all the areas of the first opening 211 and the first pixel defining layer 210 excluding the area 211A of the first opening 211, where "area" refers to an area in a plane that is parallel to the in-plane direction of the stretchable substrate 110 (e.g., a plane that is parallel to the upper surface 110S of the stretchable substrate 110).

As in above, the strain stress generated during the wet peeling of the stretchable substrate 110 may be reduced by securing the area of the first pixel defining layer 210, and according to reducing the strain stress, the deterioration of the stability and the signal sensitivity of the elements of the biosensor after peeling may be reduced or prevented.

Meanwhile, the first opening 211 is empty space where the first pixel defining layer 210 is not formed, so it is needed to secure the sufficient area of the first pixel defining layer 210 relative to the first opening 211. For example, the area 210A of the first pixel defining layer 210 excluding the first opening 211 (e.g., area 217A) may be wider (e.g., greater) than the area of the first opening 211. Restated, area 217A, which may be a difference between areas 210A and 211A, may be greater than area 211A. When the area of the pixel defining layer 210 excluding the first opening 211 is smaller than the area of the first opening 211 (e.g., when area 217A, which may be a difference between areas 210A and 211A, is smaller than area 211A), the performance of the elements may be significantly deteriorated because the strain stress is not properly controlled during the process of peeling through the wet process.

For example, the area of the first pixel defining layer 210 excluding the first opening 211 (e.g., area 217A) may be about 1.1 times or more, for example, about 1.1 times or more, about 1.2 times or more, about 1.3 times or more, about 1.4 times or more, about 1.5 times or more, about 1.6 times or more, about 1.7 times or more, about 1.8 times or more, about 1.9 times or more, about 2.0 times or more, about 3 times or more, about 4 times or more, about 5 times or more, about 6 times or more, about 7 times or more, about 8 times or more, about 9 times or more or about 10 times or more, for example about 1.1 times to about 24 times, about 1.1 times to about 23 times, about 1.1 times to about 22 times, about 1.1 times to about 21 times, about 1.1 times to about 20 times, about 1.1 times to about 19 times, about 1.1 times to about 18 times, about 1.1 times to about 17 times, about 1.1 times to about 16 times, about 1.1 times to about 15 times, about 1.1 times to about 24 times, about 1.3 times to about 24 times, about 1.5 times to about 24 times, about 1.7 times to about 24 times, about 1.9 times to about 24 times, about 2 times to about 24 times, about 3 times to about 24 times, about 4 times to about 24 times, about 5 times to about 24 times, about 6 times to about 24 times, about 7 times to about 24 times, about 8 times to about 24 times, about 9 times to about 24 times, or about 10 times to about 24 times wider (e.g., greater) than the area of the first opening 211, but the present inventive concepts are not limited thereto.

The descriptions for the aforementioned first pixel defining layer 210 and first opening 211 may be equally applied to the second pixel defining layer 220 and the second opening 212.

For example, the area 220A of the second pixel defining layer 220 may be about twice or more (e.g., equal to or greater than about 2 times), for example, about 2.4 times or more, about 2.5 times or more, about 3 times or more, about 4 times or more, about 5 times or more, about 6 times or more, about 7 times or more, about 8 times or more, about 9 times or more, or about 10 times or more, for example about 2.4 times to about 25 times, about 2.4 times to about 24 times, about 2.4 times to about 23 times, about 2.4 times to about 22 times, about 2.4 times to about 21 times, about 2.4 times to about 20 times, about 2.4 times to about 19 times, about 2.4 times to about 18 times, about 2.4 times to about 17 times, about 2.4 times to about 16 times, about 2.4 times to about 15 times, about 2.5 times to about 25 times, about 3 times to about 25 times, about 4 times to about 25 times, about 5 times to about 25 times, about 6 times to about 25 times, about 7 times to about 25 times, about 8 times to about 25 times, about 9 times to about 25 times, about 10 times to about 25 times wider (e.g., greater) than the area 212A of the second opening 212, but the present inventive concepts are not limited thereto.

The second opening 212 is empty space where the second pixel defining layer 220 is not formed, and thus it is needed to secure the sufficient area of the second pixel defining layer 220 relative to the second opening 212. For example, the area of the second pixel defining layer 220 excluding the second opening 212 (e.g., area 227A, which may be a difference between areas 220A and 212A) may be wider (e.g., the area may be greater in magnitude) than the area 212A of the second opening 212. For example, the area 220A of the second pixel defining layer 220 excluding the second opening 212 (e.g., area 227A, which may be a difference between areas 220A and 212A) may be about 1.1 times or more, about 1.2 times or more, about 1.3 times or more, about 1.4 times or more, about 1.5 times or more, about 1.6 times or more, about 1.7 times or more, about 1.8 times or more, about 1.9 times or more, about 2.0 times or more, about 3 times or more, about 4 times or more, about 5 times or more, about 6 times or more, about 7 times or more, about 8 times or more, about 9 times or more, or about 10 times or more, for example, about 1.1 times to about 24 times, about 1.1 times to about 23 times, about 1.1 times to about 22 times, about 1.1 times to about 21 times, about 1.1 times to about 20 times, about 1.1 times to about 19 times, about 1.1 times to about 18 times, about 1.1 times to about 17 times, about 1.1 times to about 16 times, about 1.1 times to about 15 times, about 1.2 times to about 24 times, about 1.3 times to about 24 times, about 1.5 times to about 24 times, about 1.7 times to about 24 times, about 1.9 times to about 24 times, about 2 times to about 24 times, about 3 times to about 24 times, about 4 times to about 24 times, about 5 times to about 24 times, about 6 times to about 24 times, about 7 times to about 24 times, about 8 times to about 24 times, about 9 times to about 24 times, or about 10 times to about 24 times wider (e.g., greater) than the area of the second opening 212, but the present inventive concepts are not limited thereto.

Similarly, for example, the entire area of the pixel defining layer 200 including the first pixel defining layer 210 and the second pixel defining layer 220 (e.g., a sum of areas 210A and 220A) may be about twice or more (e.g., equal to or greater than about twice), for example, about 2.4 times or more, about 2.5 times or more, about 3 times or more, about 4 times or more, about 5 times or more, about 6 times or more, about 7 times or more, about 8 times or more, about 9 times or more, or about 10 times or more, for example about 2.4 times to about 25 times, about 2.4 times to about 24 times, about 2.4 times to about 23 times, about 2.4 times to about 22 times, about 2.4 times to about 21 times, about 2.4 times to about 20 times, about 2.4 times to about 19 times, about 2.4 times to about 18 times, about 2.4 times to about 17 times, about 2.4 times to about 16 times, about 2.4 times to about 15 times, about 2.5 times to about 25 times, about 3 times to about 25 times, about 4 times to about 25 times, about 5 times to about 25 times, about 6 times to about 25 times, about 7 times to about 25 times, about 8 times to about 25 times, about 9 times to about 25 times, about 10 times to about 25 times wider (e.g., greater) than the areas of the first and second openings 211 and 212 (e.g., the sum of areas 211A and 212A), but the present inventive concepts are not limited thereto.

On the pixel defining layer 200, the photo-detecting element 310, and the first light emitting element 320, an encapsulant 700 is formed.

The encapsulant 700 may protect the photo-detecting element 310, the first light emitting element 320 and the pixel defining layer 200, and effectively block or reduce or prevent inflow of oxygen, moisture and/or contaminants from the outside. For example, the encapsulant 700 may reduce or prevent inflow of biological secretions such as sweats into the biosensor 10 and thus degradation of the biosensor 10.

The encapsulant 700 may cover the whole surface of the stretchable substrate 110. However, the present inventive concepts are not limited thereto, and the encapsulant 700 may be disposed separately on the first region 110A of the stretchable substrate 110, and each encapsulant 700 individually may cover the photo-detecting element 310, the first light emitting element 320, and the pixel defining layer.

The encapsulant 700 may include, for example, an organic material, an inorganic material, and/or an organic/inorganic material, and may include one or more layers. For example, the encapsulant 700 may include an oxide, a nitride, and/or an oxynitride, for example an oxide, a nitride, and/or an oxynitride including at least one of aluminum (Al), titanium (Ti), zirconium (Zr), hafnium (Hf), tantalum (Ta), or silicon (Si). For example, the encapsulant 700 may include layers having different refractive indexes that are alternately stacked. For example, a first layer including a first material selected from an oxide, a nitride, and an oxynitride, and a second layer including a second material selected from an oxide, a nitride, and an oxynitride having a higher refractive index than the first material may be alternately stacked.

Figure 3:
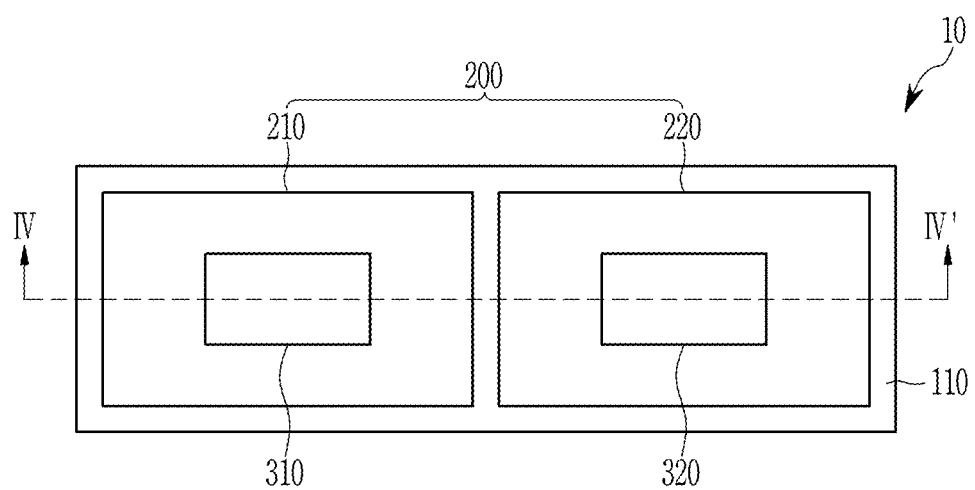
FIG. 3 is a plan view showing another example of a biosensor according to some example embodiments.
Figure 4:
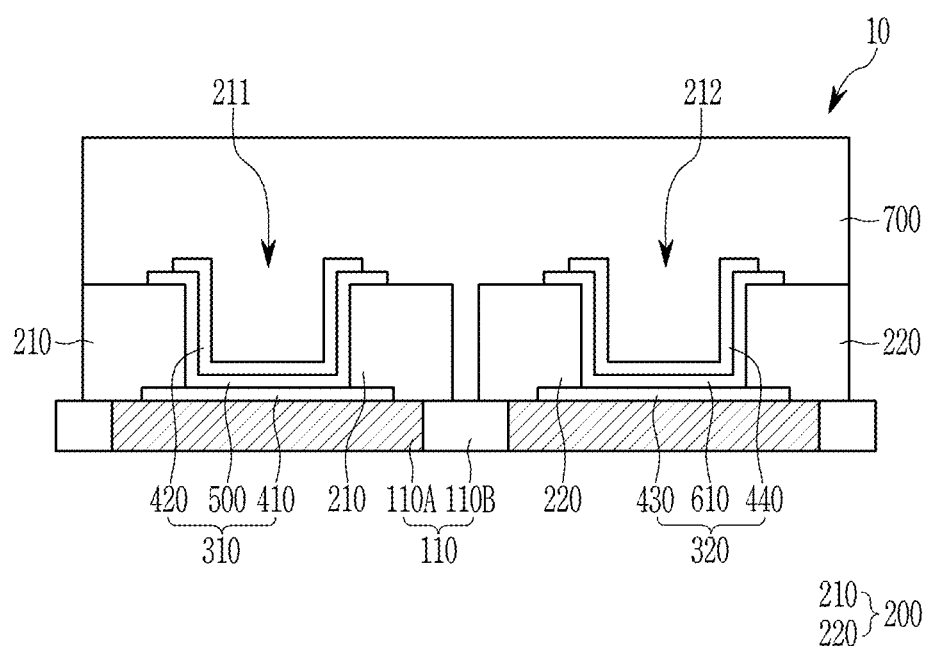
FIG. 4 is a cross-sectional view of the biosensor of FIG. 3 taken along line IV-IV'.

FIG. 3 is a plan view showing another example of a biosensor according to some example embodiments, and FIG. 4 is a cross-sectional view of the biosensor of FIG. 3 taken along line IV-IV'.

Referring to FIGS. 3 and 4, the biosensor 10 according to some example embodiments includes a stretchable substrate 110 having a first region 110A and a second region 110B, a photo-detecting element 310 including a first electrode 410, a photoelectric conversion layer 500, and a second electrode 420; a first light emitting element 320 including a third electrode 430, a first light emitting layer 610, and a fourth electrode 440; a pixel defining layer 200 having first and second openings 211 and 212; and an encapsulant 700, like some example embodiments, including the example embodiments shown in FIGS. 1 and 2.

However, in the biosensor 10 according to some example embodiments, the first pixel defining layer 210 and the second pixel defining layer 220 may be separated from each other and may be disposed in an island shape, unlike some example embodiments, including the example embodiments shown in FIGS. 1 and 2. Restated, and as shown in FIGS. 3-4, the first pixel defining layer 210 and the second pixel defining layer 220 may be isolated from direct contact with each other, for example by at least a portion of the encapsulant 700 as shown in FIG. 4 which may extend vertically between the first pixel defining layer 210 and the second pixel defining layer 220 to directly contact the upper surface 110S of the stretchable substrate 110 (e.g., an upper surface of at least a portion of a second region 110B). As the first pixel defining layer 210 and the second pixel defining layer 220 are separated as described above, flexibility of the biosensor 10 may be further increased.

Figure 5:
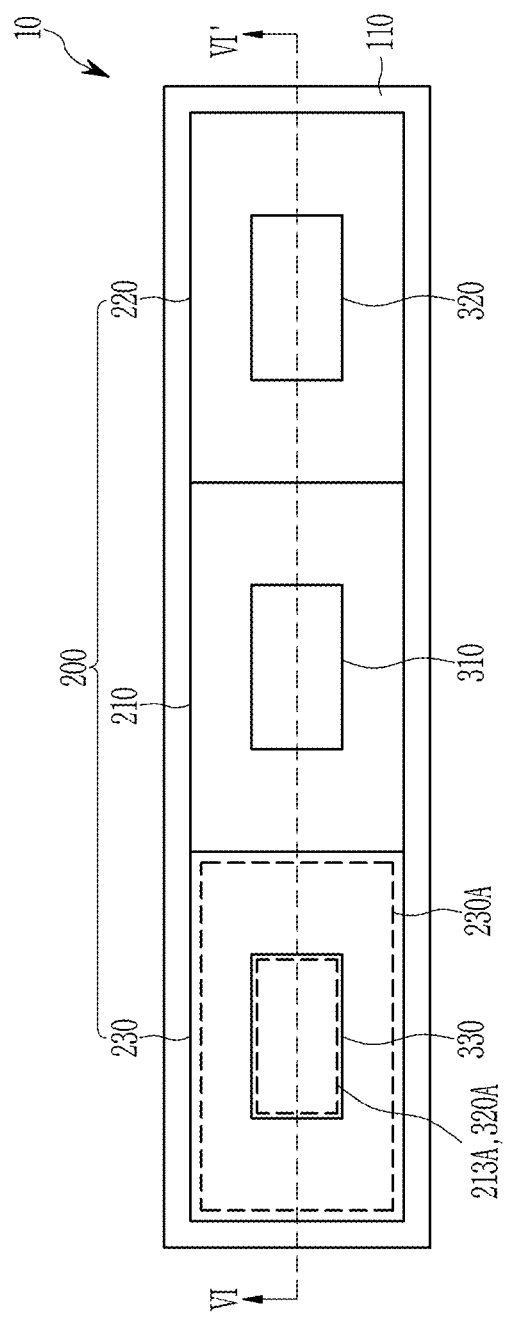
FIG. 5 is a plan view showing another example of a biosensor according to some example embodiments.
Figure 6:
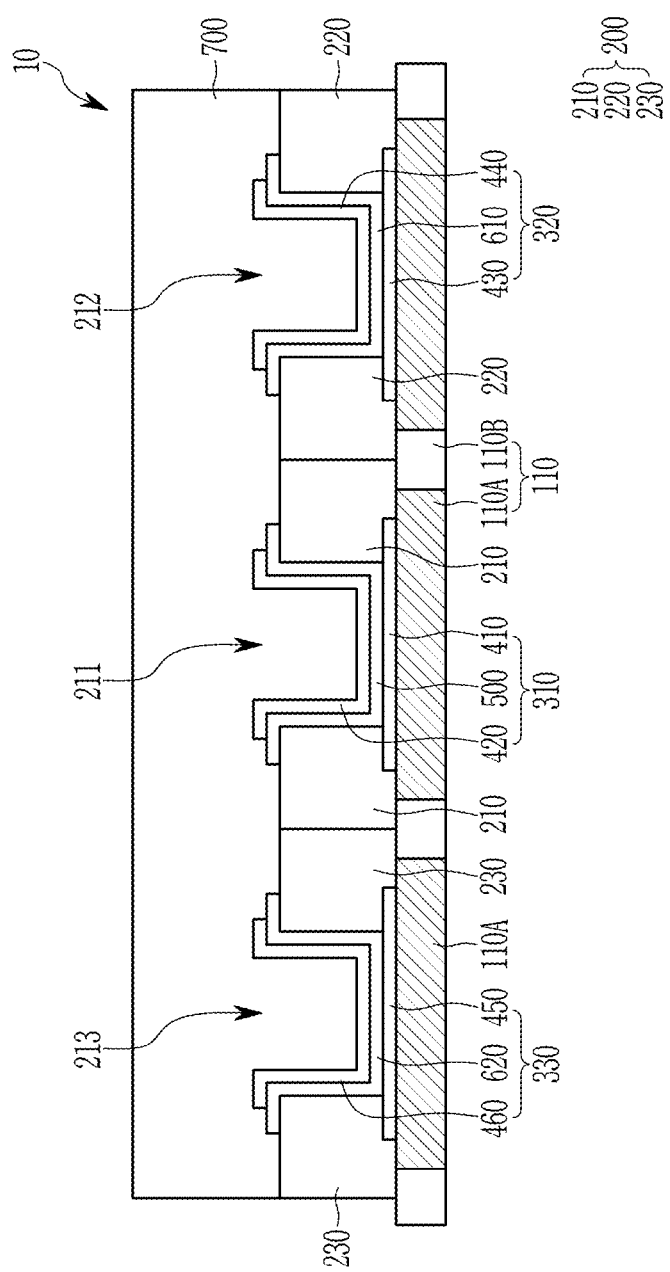
FIG. 6 is a cross-sectional view of the biosensor of FIG. 5 taken along the line VI-VI'.

FIG. 5 is a plan view showing another example of a biosensor according to some example embodiments, and FIG. 6 is a cross-sectional view of the biosensor of FIG. 5 taken along the line VI-VI'.

Referring to FIGS. 5 and 6, the biosensor 10 according to some example embodiments includes a stretchable substrate 110 having a first region 110A and a second region 110B, a photo-detecting element 310 including a first electrode 410, a photoelectric conversion layer 500, and a second electrode 420; a first light emitting element 320 including a third electrode 430, a first light emitting layer 610, and a fourth electrode 440; a pixel defining layer 200 having first and second openings 211 and 212; and an encapsulant 700, like some example embodiments, including the example embodiments shown in FIGS. 1 and 2.

However, in the biosensor 10 according to some example embodiments, unlike some example embodiments, including the example embodiments shown in FIGS. 1 and 2, the pixel defining layer 200 may further include a third pixel defining layer 230 having (e.g., including one or more inner surfaces that at least partially define) a third opening 213 and a second light emitting element 330 in (e.g., at least partially in) the third opening 213.

As shown, the third opening 213 may be at least partially defined by one or more inner surfaces of the third pixel defining layer 230 and may be further defined by a portion of the upper surface 110S of the stretchable substrate 110 that is exposed by the third opening 213 (e.g., a portion of an upper surface of the first region 110A of the stretchable substrate 110). As shown, the third opening 213 may extend through the thickness of the third pixel defining layers 230 in a vertical direction that extends perpendicular to the upper surface 110S of the stretchable substrate 110 (e.g., perpendicular to the in-plane direction of the stretchable substrate 110).

The second light emitting element 330 may include a fifth electrode 450, a sixth electrode 460, and a second light emitting layer 620 between the fifth electrode 450 and the sixth electrode 460, and the light emitting area (320A) of the second light emitting element 330 may be substantially equal to the area 213A of the third opening 213.

Meanwhile, the descriptions on the first electrode 410 and the second electrode 420 may be equally applied to the fifth electrode 450 and the sixth electrode 460.

As shown, the second light emitting element 330 may be at least partially located within the third opening 213, where portions of the second light emitting element 330 may or may not extend, in a direction parallel to the upper surface 110S, beyond the boundaries of the third opening 213. For example, as shown in FIG. 6, portions of the fifth and sixth electrodes 450 and 460 and the second light emitting layer 620 may extend in the direction parallel to the upper surface 110S beyond the lateral boundaries of the third opening 213 as at least partially defined by one or more inner surfaces of the third pixel defining layer 230. However, example embodiments are not limited thereto, and in some example embodiments the fifth and sixth electrodes 450 and 460 and the second light emitting layer 620 may be entirely located within the third opening 213 and may not extend beyond the third opening 213 in the direction parallel to the upper surface 110S.

The second light emitting layer 620 of the second light emitting element 330 may be configured to emit light in a different wavelength spectrum from the light emitted by the first light emitting layer 610 of the first light emitting element 320. The second light emitting element 330 may thus be configured to emit light having a different wavelength spectrum from light emitted by the first light emitting element 320. For example, the first light emitting layer 610 of the first light emitting element 320 may be a green light emitting element configured to emit light in a green wavelength spectrum; and the second light emitting layer 620 of the second light emitting element 330 may be a red light emitting element configured to emit light in a red wavelength spectrum, or an infrared light emitting element configured to emit light in an infrared wavelength spectrum. The green light emitting element and the red/infrared light emitting element may be, for example, employed for the absorption and/or reflection characteristics of oxyhemoglobin ($HbO_2$) and hemoglobin (Hb) in the blood vessels.

Like the aforementioned first pixel defining layer 210 and second pixel defining layer 220, the third pixel defining layer 230 may have a sufficiently large area 230A. For example, the area 230A of the third pixel defining layer 230 may be twice or more (e.g., may be equal to or greater than twice), for example, about 2.4 times to about 25 times, about 2.4 times to about 24 times, about 2.4 times to about 23 times, about 2.4 times to about 22 times, about 2.4 times to about 21 times, about 2.4 times to about 20 times, about 2.4 times to about 19 times, about 2.4 times to about 18 times, about 2.4 times to about 17 times, about 2.4 times to about 16 times, about 2.4 times to about 15 times, about 2.5 times to about 25 times, about 3 times to about 25 times, about 4 times to about 25 times, about 5 times to about 25 times, about 6 times to about 25 times, about 7 times to about 25 times, about 8 times to about 25 times, about 9 times to about 25 times, or about 10 times to about 25 times wider (e.g., greater) than the area 213A of the third opening 213, but the present inventive concepts are not limited thereto.

The aforementioned biosensor 10 may be effectively applied to the various devices or things requiring a stretchability, for example, may be applied to (e.g., included in) an attachable device such as an wearable bioelectronics; a skin-like device; or a smart clothing to provide a biometric signal or a motion signal, or may be applied to things for monitoring a strain or the like to confirm the strain change in a real time. For example, the biosensor 10 may be applied to (e.g., included in) a patch-typed or band-typed attachable biometric device (e.g., the biosensor 10 may be a skin-attachable patch typed biosensor or a skin-attachable band typed biosensor), and the attachable biometric device may be attached to a region where is required to be treated and quantitatively measured for a motion of muscle or joint to provide the needed data for rehabilitation.

For example, the above biosensor 10 may be applied in an array arranged along with a raw and/or a column.

Figure 7A:
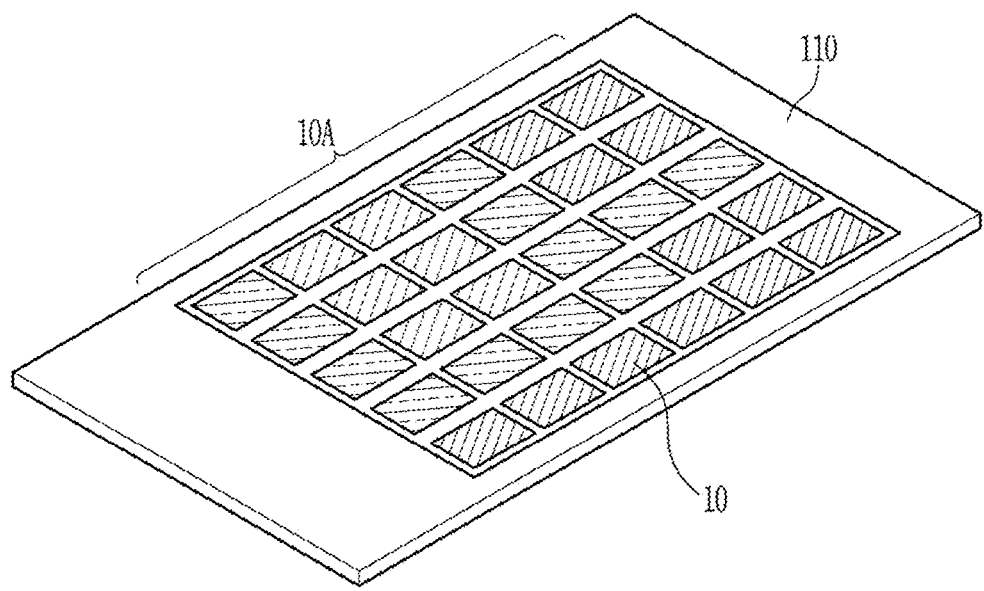
FIG. 7A is a schematic view illustrating an example of a biosensor array including a biosensor according to some example embodiments.

FIG. 7A is a schematic view illustrating an example of a biosensor array including a biosensor according to some example embodiments.

Referring to FIG. 7A, the biosensor array 10A according to some example embodiments includes a plurality of biosensors 10. The plurality of biosensors 10 is exemplified as being arranged along with a row and a column, but is not limited thereto, and may be arranged in the various ways.

For example, when the attachable biometric device including the biosensor array 10A is attached to a body area required for the treatment, it may accomplish to provide a healthcare device minimizing errors occurred depending on an attached position.

For example, the attachable biometric device including the biosensor array 10A may be attached to an area required for the treatment, and the position where strain stress occurs may be effectively detected from the muscle or joint motions to effectively provide data for rehabilitation.

Figure 7B:
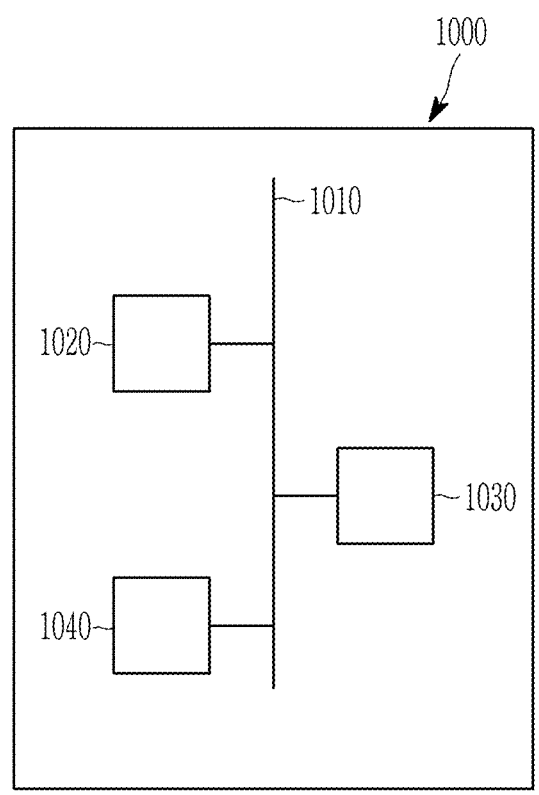
FIG. 7B is a schematic view of an electronic device according to some example embodiments.

FIG. 7B is a schematic view of an electronic device according to some example embodiments.

Referring to FIG. 7B, an electronic device 1000 (also referred to herein as a "device") may include a processor 1020, a memory 1030, and a sensor 1040 that are electrically coupled together via a bus 1010. The sensor 1040 may be any of the sensors according to any of the example embodiments (e.g., any example embodiments of biosensor 10 and/or biosensor array 10A as described herein with reference to FIGS. 1-6 and 7A). An electronic device 1000 including any of the sensors according to any of the example embodiments may be any of the attachable devices and/or stretchable devices according to any of the example embodiments, including for example an attachable biometric device as described according to any of the example embodiments. The memory 1030, which may be a non-transitory computer readable medium, may store a program of instructions. The processor 1020 may execute the stored program of instructions to perform one or more functions. For example, the processor 1020 may be configured to process electrical signals generated by the sensor 1040. The processor 1020 may be configured to generate an output (e.g., an image to be displayed on a display interface) based on such as processing.

In some example embodiments, some or all of the devices and/or elements thereof as described herein with reference to any of the drawings (including without limitation the elements of the electronic device 1000) may include, may be included in, and/or may be implemented by one or more instances of processing circuitry such as hardware including logic circuits; a hardware/software combination such as a processor executing software; or a combination thereof. For example, the processing circuitry more specifically may include, but is not limited to, a central processing unit (CPU), an arithmetic logic unit (ALU), an application processor (AP), a microcomputer, a field programmable gate array (FPGA), and programmable logic unit, a microprocessor, application-specific integrated circuit (ASIC), a neural network processing unit (NPU), an Electronic Control Unit (ECU), and the like. In some example embodiments, the processing circuitry may include a non-transitory computer readable storage device, for example a solid state drive (SSD), storing a program of instructions, and a processor (e.g., CPU) configured to execute the program of instructions to implement the functionality of any of the elements of the devices and/or elements thereof as described herein (including without limitation some or all of the electronic device 1000 shown in FIG. 7B).

Figure 8:
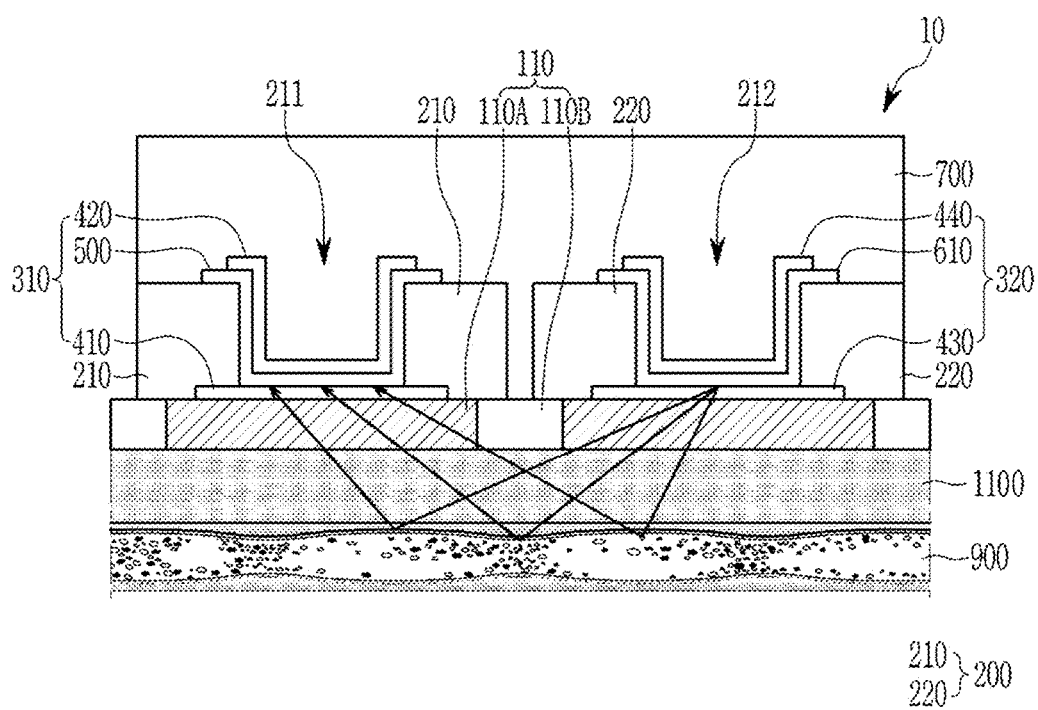
FIG. 8 is a schematic view illustrating an example of an operation of a biosensor device according to some example embodiments.

FIG. 8 is a schematic view illustrating an example of an operation of a biosensor device according to some example embodiments.

Referring to FIG. 8, the biosensor 10 includes a photoelectric conversion layer 500, a first light emitting layer 610, and a pixel defining layer 200. The biosensor 10 may detect pressure by a resistance change of a pressure sensor at a point of generating a particular (or, alternatively, predetermined) pressure such as a blood pressure, and the first light emitting layer 610 may be configured to emit light for detecting a biometric signal. Light may be reflected by a biometric (e.g., skin 1100, blood vessel 900), and the reflected light is received by a photoelectric conversion layer 500 to convert to an electrical signal. In some example embodiments, as a plurality of photoelectric conversion layers 500 adjacently disposed to each other may obtain different values depending upon a distance, the electrical signal may be treated by the various methods to enhance an accuracy of the sensor. The electrical signal converted from the reflected light may include biometric information. The electrical signal including the biometric information may be transferred to a sensor IC (not shown) or a processor (not shown).

Hereinafter, some example embodiments are illustrated in more detail with reference to examples. However, the present scope of the inventive concepts are not limited to these examples.

Evaluation of Strain Stress

The biosensors shown in FIGS. 1 and 2 are designed, and a strain stress to the photo-detecting element depending upon an area ratio of the pixel defining layer and the opening on the stretchable substrate is evaluated using a MATLAB software.

A stacked structure of the photo-detecting element is formed with IZO/organic photoelectric conversion layer/Al/encapsulation layer, and the area of the photo-detecting element is set to about 0.25 mm$^2$ (0.5 mm×0.5 mm).

The results are shown in Table 1.

TABLE 1

| Area of pixel defining layer/<br>Area of opening | Strain stress<br>(unit: %) |
| --- | --- |
| 1.2 | 0.81 |
| 2 | 0.60 |
| 2.4 | 0.5 |
| 3 | 0.32 |
| 4 | 0.26 |

Referring to Table 1, the strain stress of the photo-detecting element is changed depending upon an area ratio of the pixel defining layer and the opening, and it may be expected that deformation of the element due to the strain stress may be reduced or prevented when the area of the pixel defining layer is about twice or more the area of the opening.

Manufacture of Biosensor

Example 1

A SEBS polymer is coated on a glass substrate and dried to provide a stretchable substrate. A metal wire which is used as an electric transferring path is formed on the stretchable substrate. Then indium zinc oxide (IZO) is sputtered on the stretchable substrate at a room temperature to provide electrodes. Subsequently, a photosensitive polymer of GXR601 is coated on the electrodes and the stretchable substrate to form a pixel defining layer, and then the pixel defining layer is patterned through a fine patterning process to form a first pixel defining layer having a first opening and a second pixel defining layer having a second opening.

In some example embodiments, each area of the first and the second pixel defining layers is 1 mm$^2$, and each area of the first and the second opening is 0.25 mm$^2$.

A lower electrode (IZO)/a hole auxiliary layer/an organic light emitting layer/an electron auxiliary layer/a upper electrode (Al) are sequentially stacked on the stretchable substrate to provide a red light emitting element (area: 0.5×0.5 mm²), and a lower electrode (IZO)/a hole auxiliary layer/a light absorbing layer (SubNc/C60)/an electron auxiliary layer/an upper electrode (Al) are sequentially stacked to provide a photo-detecting element (area: 0.5×0.5 mm²). Subsequently, a fluoro-based polymer and aluminum oxide (AlO$_x$) are sequentially coated on the red light emitting element and the photo-detecting element to form an organic-inorganic hybrid bilayer-type encapsulant, manufacturing a biosensor according to Example 1.

Comparative Example 1

A biosensor is manufactured in accordance with the same procedure as in Example 1, except that each area of the first pixel defining layer and the second pixel defining layer of the biosensor is formed in 0.325 mm².

Evaluation 1: Measurement of Photoelectric Conversion Efficiency and Dark Current Density After measuring an external quantum efficiency (EQE) and a dark current density of the biosensors according to Example 1 and Comparative Example 1, the biosensors according to Example 1 and Comparative Example 1 are immersed in water for about 4 hours to about 5 hours and taken out therefrom, the biosensor (the stretchable substrate of the biosensor) is separated from the glass substrate, and then an external quantum efficiency (EQE) and the dark current density of the biosensors are measured in order to confirm the change of the external quantum efficiency (EQE) and the dark current density.

The external quantum efficiency (EQE) is evaluated at a wavelength of 650 nm according to an Incident Photon to Current Efficiency (IPCE) method.

The dark current density is evaluated from a dark current density in which a dark current measured using a current-voltage evaluating equipment (Keithley K4200 parameter analyzer) is divided by a unit pixel area. The dark current density is evaluated from a flowing current when a −2V to 2V bias is applied.

The results are shown in FIGS. 9A, 9B, 10A, and 10B.

Figure 9A:
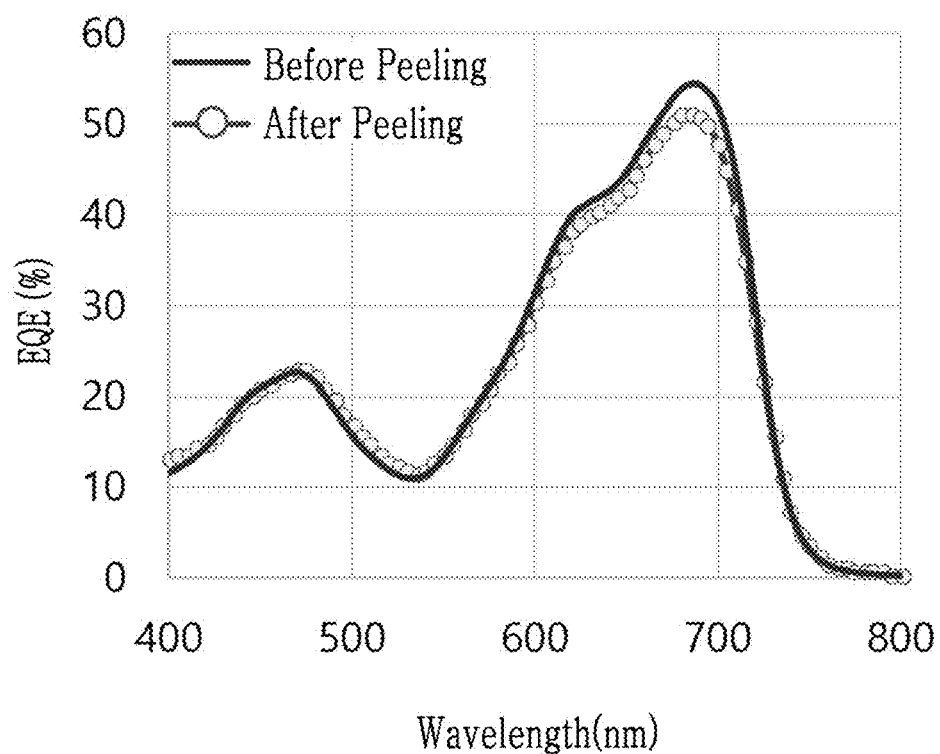
FIG. 9A is a graph showing a measurement result of photoelectric conversion efficiency before and after peeling a thin film of the biosensor according to Example 1 according to some example embodiments.
Figure 9B:
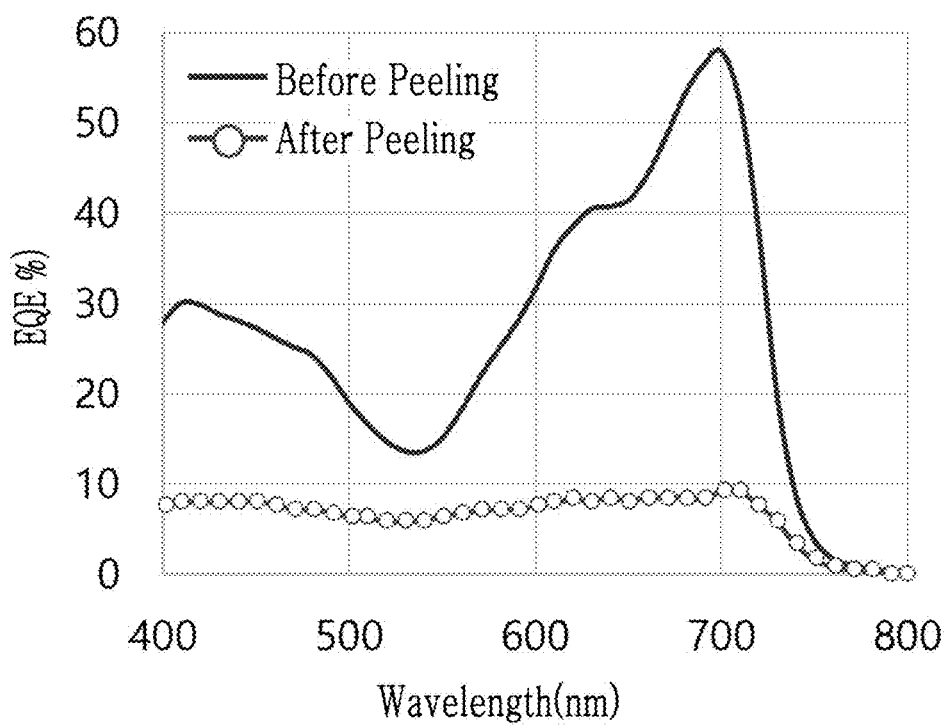
FIG. 9B is a graph showing a measurement result of photoelectric conversion efficiency before and after peeling a thin film of the biosensor according to Comparative Example 1 according to some example embodiments.
Figure 10A:
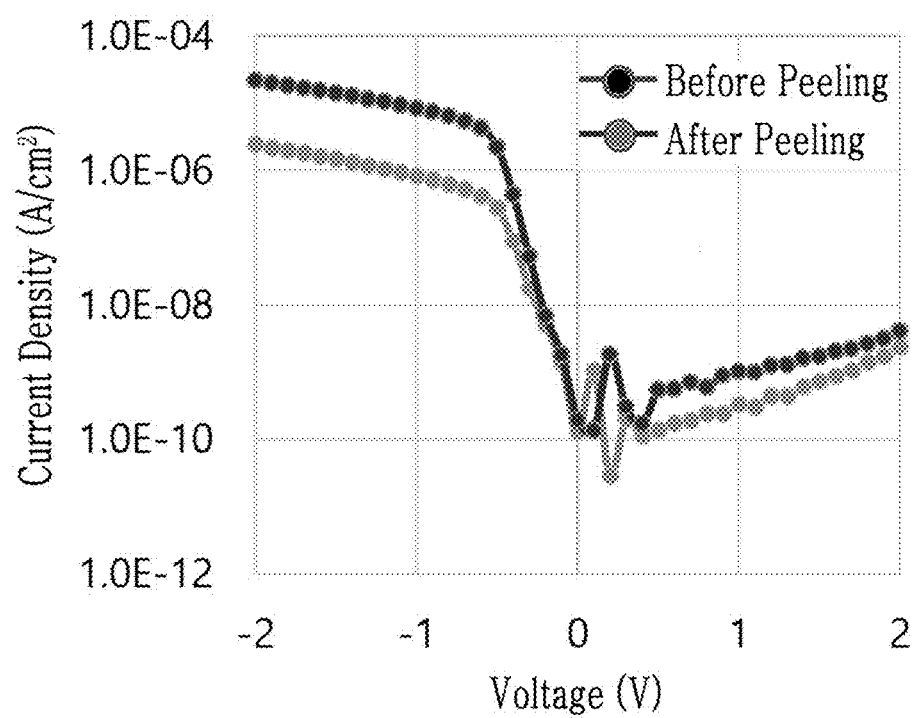
FIG. 10A is a graph showing a dark current density according to an applied voltage before and after peeling a thin film of the biosensor according to Example 1 according to some example embodiments.
Figure 10B:
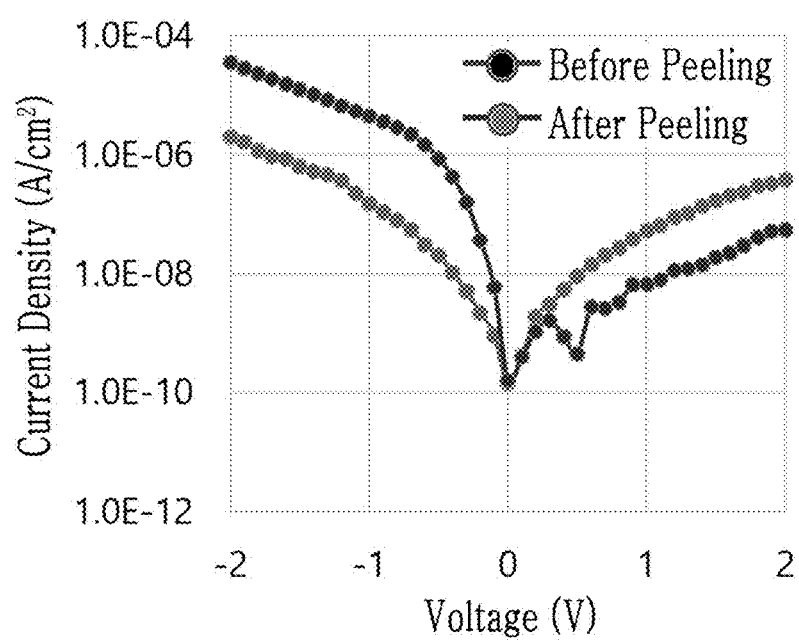
FIG. 10B is a graph showing a dark current density according to an applied voltage before and after peeling a thin film of the biosensor according to Comparative Example 1 according to some example embodiments.

FIG. 9A is a graph showing the external quantum efficiency (EQE) according to the wavelength of the biosensor according to Example 1, FIG. 9B is a graph showing the external quantum efficiency (EQE) according to the wavelength of the biosensor according to Comparative Example 1, FIG. 10A is a graph showing the dark current density according to the applied voltage before and after peeling of the stretchable substrate of the biosensor according to Example 1, and FIG. 10B is a graph showing the dark current density according to the applied voltage before and after peeling of the stretchable substrate of the biosensor according to Comparative Example 1.

Referring to FIGS. 9A and 10A, the external quantum efficiency (EQE) and the dark current density of the photo-detecting element of the biosensor according to Example 1 are not substantially changed before and after peeling process.

On the other hand, referring to FIGS. 9B and 10B, the external quantum efficiency (EQE) of the photo-detecting element of the biosensor according to Comparative Example 1 is significantly changed before and after peeling process, and particularly, the value is greatly decreased to a level of 20% relative to the value before peeling process at a wavelength of around 650 nm, and the change of the dark current density of the photo-detecting element before and after peeling process is also large.

Evaluation 2: SNR Measurement

The biosensors according to Example 1 and Comparative Example 1 are attached to a region near to a radial artery of the wrist and measured for a signal to noise ratio (SNR), and then the biosensors according to Example 1 and Comparative Example 1 are immersed in water for about 4 hours to 5 hours and taken out to separate the stretchable substrate from the glass substrate, and then attached to the region near to the radial artery of the wrist and measured for the signal to noise ratio (SNR) of the biosensors to confirm the change of the signal to noise ratio.

SNR signal data is collected using an AFE software.

Figure 11A:
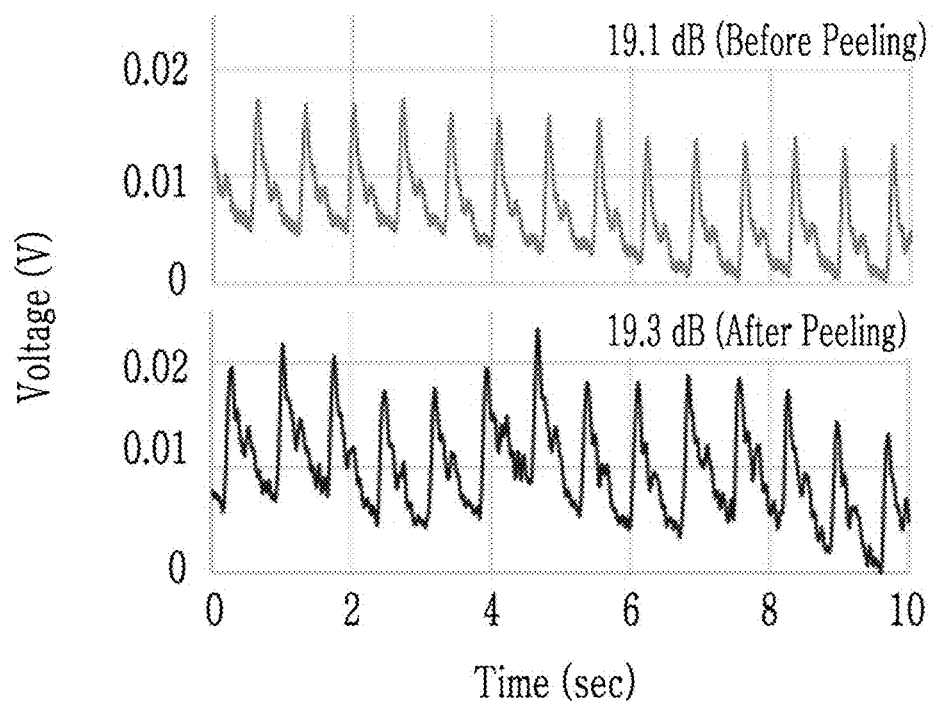
FIG. 11A is a graph showing SNR measurement results before and after peeling a thin film of the biosensor according to Example 1 according to some example embodiments.
Figure 11B:
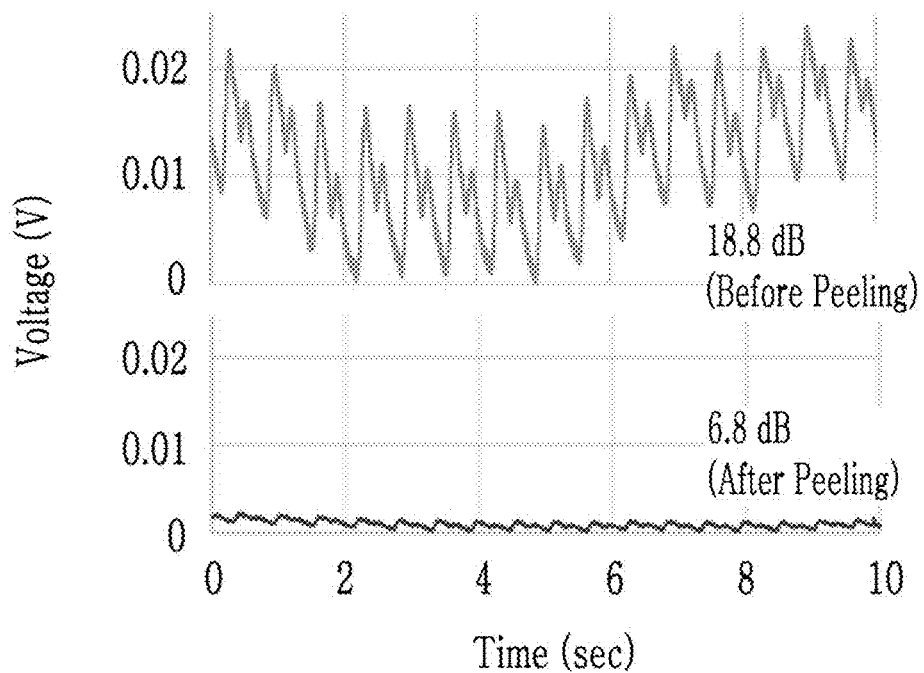
FIG. 11B is a graph showing SNR measurement results before and after peeling a thin film of the biosensor according to Comparative Example 1 according to some example embodiments.

The results are shown in FIGS. 11A and 11B.

FIG. 11A is a graph showing a biosignal before and after the peeling process of the biosensor according to Example 1 and FIG. 11B is a graph showing a biosignal before and after the peeling process of the biosensor according to Comparative Example 1.

Referring to FIG. 11A, the biosensor according to Example 1 has substantially no change in the SNR value before and after the peeling process, and thus the performance of the photo-detecting element before and after peeling process is well maintained.

On the other hand, referring to FIG. 11B, the biosensor according to Comparative Example 1 exhibits SNR values of 18.8 dB and 6.8 dB before and after the peeling process, respectively, which indicates that it has been greatly deteriorated after the peeling process.

From these results, the strain stress of the element after the peeling process by the wet process is varied depending upon a relative area of the pixel defining layer, and the performance degradation of the element does not occur in the biosensor according to Example 1 having a relatively wider (e.g., relatively greater) area of the pixel defining layer than the biosensor according to Comparative Example 1 having a relatively smaller area of the pixel defining layer.

While the inventive concepts have been described in connection with what is presently considered to be practical example embodiments, it is to be understood that the inventive concepts are not limited to these example embodiments. On the contrary, the inventive concepts are intended to cover various modifications and equivalent arrangements included within the spirit and scope of the appended claims.

What is claimed is:

1. A biosensor, comprising:
   a stretchable substrate,
   a pixel defining layer on the stretchable substrate, the pixel defining layer including
      a first pixel defining layer defining a first opening extending through a thickness of the first pixel defining layer, and
      a second pixel defining layer defining a second opening extending through
   a thickness of the second pixel defining layer,
   a photo-detecting element at least partially in the first opening, and
   a first light emitting element at least partially in the second opening,
   wherein an area of the first pixel defining layer in a plane parallel to an in-plane direction of the stretchable substrate is about 2 times to about 25 times an area of the first opening in the plane parallel to the in-plane direction of the stretchable substrate.

2. The biosensor of claim 1, wherein the area of the first pixel defining layer is about 2.4 times to about 25 times the area of the first opening.

3. The biosensor of claim 1, wherein the area of the first pixel defining layer excluding the first opening is greater than the area of the first opening.

4. The biosensor of claim 3, wherein the area of the first pixel defining layer excluding the first opening is about 1.1 times to about 24 times the area of the first opening.

5. The biosensor of claim 1, wherein the first pixel defining layer excluding the first opening is in direct contact with the stretchable substrate.

6. The biosensor of claim 1, wherein an area of the second pixel defining layer is equal to or greater than about twice an area of the second opening.

7. The biosensor of claim 1, wherein an area of the second pixel defining layer excluding the second opening is greater than an area of the second opening.

8. The biosensor of claim 1, wherein the second pixel defining layer excluding the second opening is in direct contact with the stretchable substrate.

9. The biosensor of claim 1, wherein
the first pixel defining layer and the second pixel defining layer are connected to each other, and
a boundary between the first pixel defining layer and the second pixel defining layer located halfway along a gap between an edge of the first opening and an edge of the second opening facing each other.

10. The biosensor of claim 9, wherein a magnitude of the gap between the edge of the first opening and the edge of the second opening facing each other is about 0.4 times to about 4 times a magnitude of a width of the first opening or a width of the second opening in a direction extending parallel to a direction of the gap.

11. The biosensor of claim 1, wherein the area of the pixel defining layer is equal to or greater than about twice a sum of the area of the first opening and an area of the second opening.

12. The biosensor of claim 1, wherein
the photo-detecting element includes
a first electrode and a second electrode facing each other, and
a photoelectric conversion layer between the first electrode and the second electrode, and
an area of an active region of the photo-detecting element is substantially equal to the area of the first opening.

13. The biosensor of claim 1, wherein
the first light emitting element includes
a third electrode and a fourth electrode facing each other, and
a light emitting layer between the third electrode and the fourth electrode, and
a light emitting area of the first light emitting element is substantially equal to an area of the second opening.

14. The biosensor of claim 1, wherein the first pixel defining layer and the second pixel defining layer are isolated from direct contact with each other.

15. The biosensor of claim 1, wherein
the pixel defining layer further includes a third pixel defining layer at least partially defining a third opening extending through a thickness of the third pixel defining layer, and
the biosensor further includes a second light emitting element at least partially in the third opening.

16. The biosensor of claim 15, wherein an area of the third pixel defining layer is equal to or greater than about twice an area of the third opening.

17. The biosensor of claim 15, wherein the second light emitting element is configured to emit light having a different wavelength spectrum from light emitted by the first light emitting element.

18. The biosensor of claim 1, wherein
the stretchable substrate includes a plurality of first regions and a second region between adjacent first regions of the plurality of first regions, the first regions having a first stiffness and the second region having a second stiffness that is lower than the first stiffness, and
the photo-detecting element and the first light emitting element are on separate, respective first regions of the plurality of first regions.

19. The biosensor of claim 1, wherein the biosensor is a skin-attachable patch typed biosensor or a skin-attachable band typed biosensor.

20. A biosensor array comprising the biosensor of claim 1.

21. A device comprising the biosensor of claim 1.

* * * * *